(12) United States Patent
Omura

(10) Patent No.: US 11,096,872 B2
(45) Date of Patent: Aug. 24, 2021

(54) WATER-IN-OIL EMULSION COSMETIC MATERIAL

(71) Applicant: SHISEIDO COMPANY, LTD., Tokyo (JP)

(72) Inventor: Takayuki Omura, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 242 days.

(21) Appl. No.: 16/069,979

(22) PCT Filed: Dec. 12, 2016

(86) PCT No.: PCT/JP2016/086853
§ 371 (c)(1),
(2) Date: Jul. 13, 2018

(87) PCT Pub. No.: WO2017/126252
PCT Pub. Date: Jul. 27, 2017

(65) Prior Publication Data
US 2019/0038526 A1 Feb. 7, 2019

(30) Foreign Application Priority Data
Jan. 18, 2016 (JP) .............................. JP2016-007211

(51) Int. Cl.
| | | |
|---|---|---|
| A61K 8/06 | (2006.01) | |
| A61Q 19/00 | (2006.01) | |
| A61Q 13/00 | (2006.01) | |
| A61K 8/894 | (2006.01) | |
| A61K 8/893 | (2006.01) | |
| A61K 8/41 | (2006.01) | |
| A61K 8/26 | (2006.01) | |
| A61K 8/25 | (2006.01) | |

(52) U.S. Cl.
CPC .............. *A61K 8/06* (2013.01); *A61K 8/064* (2013.01); *A61K 8/25* (2013.01); *A61K 8/26* (2013.01); *A61K 8/416* (2013.01); *A61K 8/893* (2013.01); *A61K 8/894* (2013.01); *A61Q 13/00* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 7,226,901 B2 * | 6/2007 | Stora ........................ | A61K 8/70 512/1 |
| 2004/0116323 A1 | 6/2004 | Stora | |
| 2015/0231043 A1 * | 8/2015 | Sasaki ..................... | A61K 8/585 424/59 |

FOREIGN PATENT DOCUMENTS

| | | |
|---|---|---|
| CN | 104768529 A | 7/2015 |
| EP | 2 481 394 | 9/2010 |
| EP | 2 965 743 | 3/2014 |
| JP | H0380531 | 2/1991 |
| JP | 2000-072646 | 3/2000 |
| JP | B3524717 | 5/2004 |
| JP | B5384050 | 1/2014 |
| WO | WO2009/119000 | 10/2009 |
| WO | WO2013/024653 | 2/2013 |
| WO | WO2014/069173 | 5/2014 |

OTHER PUBLICATIONS

PCT/JP2016/086853 International Search Report and Written Opinion, dated Feb. 17, 2017, 5 page—English, 6 pages—Japanese.
EP 16886491.6, Extended European Search Report dated Jul. 4, 2019, 9 pages—English.
ABIL®EM 90, Emulsififer for the formulation of cosmetic W/O creams and lotions, Degussa. XP007906324, Goldschmidt TmbH, Germany, dated May 2003, www.degussa-personal-care.com, 8 pages—English.
CN Appln. No. 201680078938.2, Chinese Office Action dated Aug. 14, 2020, 17 pages—Chinese; 8 pages—Japanese; 5 pages—English.

* cited by examiner

*Primary Examiner* — Tigabu Kassa
(74) *Attorney, Agent, or Firm* — Andrew F. Young, Esq.; Nolte Lackenback Siegel

(57) ABSTRACT

A water-in-oil emulsion cosmetic, has good stability and does not cause a decrease in viscosity when a large quantity of fragrance material is blended. The water-in-oil emulsion cosmetic, includes: (a) 5 to 15% by mass of a fragrance material, (b) 1.5 to 3% by mass of dimethyldistearylammonium hectorite, and, (c) a nonionic surfactant, wherein, the (c) nonionic surfactant comprises (c1) 2 to 10% by mass relative to the total weight of the composition of a polyether modified silicone having a C12-22 branched hydrocarbon chain, and may comprise (c2) 10% by mass or less relative to the total weight of the composition of a polyether modified silicone having no alkyl chain, wherein, a ratio of the total blending quantity of the component (c1) and the component (c2) relative to a blending quantity of the component (b) is 2 or more, a ratio of the total blending quantity of the component (c1) and the component (c2) to a blending quantity of the component (a) is 0.8 or more, the total blending quantity of the component (c1) and the component (c2) is 4% by mass or more, a ratio of a blending quantity of the component (c1) to that of the component (c2) is 0.8 or more, and the composition has a hardness of 6 or more as measured using a rheometer.

4 Claims, No Drawings

WATER-IN-OIL EMULSION COSMETIC MATERIAL

CROSS REFERENCE TO RELATED APPLICATIONS

This application relates to and claims priority as a § 371 national phase, from PCT/JP2016/086853 filed Dec. 12, 2016, the entire contents of which are incorporated herein by reference, which in turn claims priority from JP 2016-007211 filed Jan. 18, 2016.

Figure Selected for Publication

None

TECHNICAL FIELD

The present invention relates to a water-in-oil (type) emulsion cosmetic. More specifically, the present invention relates to a stable water-in-oil emulsion cosmetic, which can retain appropriate hardness without causing a decrease in viscosity even when fragrance materials are blended therein in a large quantity.

BACKGROUND ART

Water-in-oil emulsion cosmetics have water resistance better than that of oil-in-water emulsion cosmetics, have properties such that an emollient oil, an oil-soluble agent, a UV absorbent and the like can be efficiently blended therein, and thus can be cosmetics having high skincare effects. However, the water-in-oil emulsion cosmetics may be problematic in that the stabilization is more difficult than oil-in-water emulsion cosmetics, and they have poor freshness, and creates the senses of use such as a sticky feeling and an oily feeling.

An emulsion is stabilized by thickening or gelating oils constituting the external phase (oil phase) of a water-in-oil emulsion cosmetic. For example, it is known that an organic modified clay mineral prepared by treating a water swellable clay mineral with a quaternary ammonium salt cationic surfactant and a nonionic surfactant can constitute a stable water-in-oil emulsion cosmetic as an emulsifying agent (Patent document 1).

Since the emulsion system described in Patent document 1 can maintain a stable water-in-oil emulsion system even when water is blended therein in a large quantity, its application has been attempted to a skincare cosmetic or a makeup cosmetic that has a fresh sense of use, although it is a water-in-oil emulsion type. For example, Patent document 2 discloses a water-in-oil emulsion cosmetic containing ethanol and a freshener, and having fresh and plain senses of use and freshness. Furthermore, Patent document 3 describes a gelatinous cosmetic, and particularly a makeup cosmetic, having fresh and unique soft texture.

Meanwhile, a cosmetic such as cream is scented with a fragrance material to enhance the attractiveness of the product. The quantity of the fragrance material to be blended in a water-in-oil emulsion cosmetic such as cream in general is at most 1% by mass, and generally from about 0.1% by mass to 0.5% by mass (for example, see Examples 7 and 9 of Patent document 1). Even when a water-in-oil emulsion cosmetic has been stabilized by emulsification using the above organic modified clay mineral, blending a fragrance material in a large quantity (for example, in a quantity of 5% by mass or more) in the water-in-oil emulsion cosmetic results in a problem such that a decrease in viscosity leads to destabilization.

CITATION LIST

Patent Document

Patent document 1: JP-A H03-80531
Patent document 2: JP-B 3524717
Patent document 3: JP-B 5384050

SUMMARY OF THE INVENTION

Problem to be Solved by the Invention

An object of the present invention is to provide a water-in-oil emulsion cosmetic, which has good stability such that it does not cause a decrease in viscosity even when a fragrance material is blended in a large quantity therein.

Means for Solving the Problem

As a result of intensive studies to achieve the above object, the present inventors have discovered that a stable water-in-oil emulsion cosmetic, which does not cause a decrease in viscosity even when a fragrance material is blended therein in a large quantity, is obtained by blending dimethyldistearylammonium hectorite and a nonionic silicone-based surfactant having a specific structure in combination, and setting the ratios of the blending quantities of the components within a specific range, and thus have completed the present invention.

Specifically, the present invention provides a water-in-oil emulsion composition, comprising:
(a) 5 to 15% by mass of a fragrance material,
(b) 1.5 to 3% by mass of dimethyldistearylammonium hectorite, and,
(c) a nonionic surfactant,
wherein, the (c) nonionic surfactant comprises (c1) 2 to 10% by mass relative to the total weight of the composition of a polyether modified silicone having a C12-22 branched hydrocarbon chain, and may comprise (c2) 10% by mass or less relative to the total weight of the composition of a polyether modified silicone having no alkyl chain,
wherein, a ratio of the total blending quantity of the component (c1) and the component (c2) relative to a blending quantity of the component (b), i.e., [((c1)+(c2))/(b)], is 2 or more, wherein, a ratio of the total blending quantity of the component (c1) and the component (c2) to a blending quantity of the component (a), i.e., [((c1)+(c2))/(a)], is 0.8 or more,
wherein, the total blending quantity of the component (c1) and the component (c2) is 4% by mass or more, wherein, a ratio of a blending quantity of the component (c1) to that of the component (c2), i.e., [(c1)/(c2)], is 0.8 or more, and
wherein, the composition has a hardness of 6 or more as measured using a rheometer (11.3 φ, 3 mm penetration) at 25° C.;
as well as a water-in-oil emulsion cosmetic comprising the above-described composition.

Effects of the Invention

The water-in-oil emulsion cosmetic of the present invention is stable, and maintains appropriate hardness without causing any decrease in viscosity even when a fragrance material is blended therein in a quantity as high as 5% by mass or higher, and exerts a fresh sense of use. The water-in-oil emulsion cosmetic has a highly scented fragrant effect so as to be able to produce a luxurious feel similar to that of fragrance cosmetics such as perfumes and eau de cologne, since a fragrance material is blended in a high quantity compared to that in conventional cream or the like.

DESCRIPTION OF EMBODIMENTS

The water-in-oil emulsion cosmetic of the present invention (hereinafter, may also simply referred to as "emulsion cosmetic") contains 5 to 15% by mass of a fragrance material (component (a)). Fragrance materials to be blended in cosmetic is generally classified into natural fragrance (natural aromatic), synthetic fragrance (synthetic perfume) and compounded fragrance (compounded perfume). Natural fragrance is fragrance containing a component originated from a plant or an animal as a major component. Examples of plant origin natural fragrances include rose oil, jasmine oil, neroli oil, lavender oil, ylang ylang oil, tuberose oil, clary sage oil, clove oil, peppermint oil, geranium oil, patchouli oil, sandalwood oil, cinnamon oil, coriander oil, nutmeg oil, pepper oil, lemon oil, orange oil, bergamot oil, opoponax oil, vetiver oil, orris oil, oak moss oil and so forth. Examples of animal origin natural fragrances include musk oil, civet oil, castoreum oil, ambergris oil and so forth.

Synthetic fragrances are sometimes being classified into hydrocarbon, alcohol, aldehyde, ketone, ester, lactone, phenol, acetal and the like in view of their chemical structures or osmophore groups. Specific examples thereof include limonene and β-caryophyllene, (as a hydrocarbon); cis-3-hexenol, linalol, farnesol, β-phenylethyl alcohol, geraniol, citronellol, terpineol, menthol, santalol, bacdanol and brahmanol (as an alcohol); 2,6-nonadienal, citral, α-hexyl cinnamaldehyde, lyral and lilial (as an aldehyde); 1-carvon, cyclopentadecanone, β-ionone, damascone, methyl ionone, irone, iso-E-super, acetylcedrene and muscone, (as a ketone); linalyl acetate, benzyl benzoate, benzyl acetate, methyl dihydroxy jasmonate and methyl jasmonate (as an ester); γ-undecalactone, Jasmine lactone, cycropentadecanolide and ethylene brassylate (as a lactone); eugenol (as a phenol); phenylacetaldehyde dimethyl acetal (as an acetal); rose oxide; indole; aurantiol; and so forth.

Compounded fragrance is a fragrance (mixed aroma-chemicals) obtained by compounding natural fragrance and/or synthetic fragrance, and a material having fragrant function as its main body is referred to as base fragrance for compounding. As basic base fragrance, floral fragrance such as rose, jasmine, and muguet, woody, chypre, citrus, green, fougere, and oriental aromas are known, for example. Furthermore, as base fragrance for producing a rich note (taste) and broaden note (taste) of fragrance through addition thereof in small quantities, fruity, spicy, aldehyde, and animal aromas, and the like are also known.

The fragrance material in the present invention is at least one selected from the above natural fragrances, synthetic fragrances, and compounded fragrances, and is not particularly limited.

The blending quantity of fragrance material in the emulsion cosmetic of the present invention ranges from 5 to 15% by mass, preferably 5 to 12% by mass, and more preferably 5 to 10% by mass. Scenting and perfuming (fragrant) effects cannot be obtained as intended when the blending quantity is less than 5% by mass. The blending quantity of more than 15% by mass may lead to excessively strong scent or may adversely affect the emulsion stability.

The water-in-oil emulsion cosmetic according to the present invention contains dimethyldistearylammonium hectorite (component (b)).

The dimethyldistearylammonium hectorite (component (b)) in the present invention is one organic modified clay minerals that have been conventionally used as an oil-phase thickener (or gelling agent) such as a cosmetic, and forms a composite with a nonionic surfactant in oil to form an oil gel (see Patent documents 1 to 3).

A commercially available product can be used as the dimethyldistearylammonium hectorite (component (b)) in the present invention, and examples thereof can include "BENTONE 38V" and "BENTONE 38VCG" (e.g., Elementis Japan KK).

The blending quantity of the dimethyldistearylammonium hectorite (component (b)) in the emulsion cosmetic of the present invention ranges from 1.5 to 3.0% by mass, preferably 1.8 to 2.8% by mass, and more preferably 2.0 to 2.5% by mass. If the blending quantity of the component (b) is less than 1.5% by mass, sufficient emulsion stability cannot be obtained.

The emulsion cosmetic of the present invention contains a nonionic surfactant ((c) component) that forms a composite with the above dimethyldistearylammonium hectorite (component (b)).

The nonionic surfactant in the present invention contains polyether modified silicone having a C12-22 branched hydrocarbon chain (component (c1)).

The polyether modified silicone having a C12-22 branched hydrocarbon chain (component (c1)) has a polyoxyalkylene group and a C12-22 hydrocarbon group, preferably an alkyl group in the side chains of the linear or branched silicone backbone, and includes those also referred to as polyether-alkyl-comodified silicone. An example thereof is polyether-alkyl-comodified silicone having a structure represented by the following general formula (I).

[Chemical formula 1]

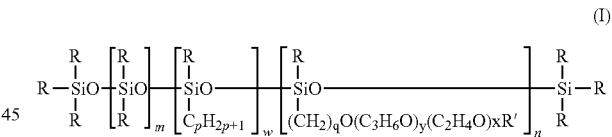

In the above formula (I),

R is a C1-3 alkyl group or a phenyl group (preferably a methyl group);

R' is hydrogen or a C1-12 alkyl group (preferably hydrogen);

p ranges from 12 to 22 (preferably 10 to 18, particularly preferably 12 to 16);

q ranges from 1 to 50 (preferably 3);

m ranges from 1 to 100;

n, w and x range respectively from 1 to 50; and y ranges from 0 to 50.

Note that the order for adding polyoxyethylene and polyoxypropylene is not particularly limited and may be a random or block order. In addition, examples of the alkyl chain ($C_pH_{2p+1}$) include a linear or branched chain.

Specific examples thereof include methyl polysiloxane-cetylmethylpolysiloxane-poly(oxyethylene•oxypropylene) methylpolysiloxane copolymer (also be referred to as cetyldimethicone copolyol) having a linear silicone backbone, and as a commercially available product, ABIL EM90

(manufactured by Degussa). Moreover, lauryl PEG-9 polydimethylsiloxyethyldimethicone (KF-6038; manufactured by Shin-Etsu Chemical Co., Ltd.) having a branched silicone backbone and the like can also be used herein.

The blending quantity of polyether modified silicone having a C12-22 branched hydrocarbon chain (component (c1)) in the emulsion cosmetic of the present invention ranges from 2 to 10% by mass, preferably 2 to 8% by mass, and more preferably 2 to 6% by mass relative to the total weight of the cosmetic.

The nonionic surfactant in the present invention ((c) component) may further contain at least one selected from polyether modified silicone having no alkyl chain (component (c2)). Such polyether modified silicone having no alkyl chain is generally referred to as simply polyether-modified silicone.

Polyether-modified silicone to be used in the present invention has a polyoxyalkylene group in the side chains of a linear or branched silicone backbone, and examples thereof include those represented by the following general formula (II).

[Chemical formula 2]

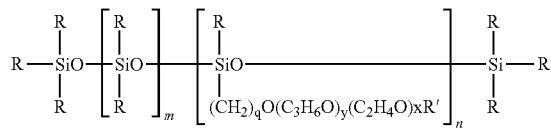

(II)

In the above formula (II),
R is a C1-3 alkyl group or a phenyl group (preferably a methyl group);
R' is hydrogen or a C1-12 alkyl group (preferably hydrogen or a methyl group);
q ranges from 1 to 50 (preferably 3);
m ranges from 1 to 100;
n and x range respectively from 1 to 50; and
y ranges from 0 to 50.

Note that the order of adding polyoxyethylene and polyoxypropylene is not particularly limited, and may be a random or block order.

As polyether-modified silicone (component (c2)) in the present invention, polyether-modified silicone having a branched silicone backbone (may also be referred to as branched-chain-type polyether-modified silicone) is particularly preferable. Specific examples of such a branched-chain-type polyether-modified silicone include PEG-9 polydimethylsiloxyethyldimethicone, and as a commercially available product, KF-6028 (manufactured by Shin-Etsu Chemical Co., Ltd.). Specific examples of the same having a linear silicone backbone (linear-type polyether-modified silicone) include PEG-10 dimethicone, and as a commercially available product, KF-6017 or KF-6017P (manufactured by Shin-Etsu Chemical Co., Ltd.).

The blending quantity of the polyether modified silicone having no alkyl chain (component (c2)) in the emulsion cosmetic of the present invention is 10% by mass or less (0 to 10% by mass), preferably 1 to 6% by mass, and more preferably 2 to 4% by mass relative to the total weight of the cosmetic.

Note that the component (c2) in the present invention is not an essential component, and the emulsion cosmetic of the present invention includes an embodiment in which no component (c2) is contained. However, in the emulsion cosmetic of the present invention, the total blending quantity of the component (c1) and the component (c2) is required to be 4% by mass or higher. Specifically, when the blending quantity of the component (c1) is less than 4% by mass, the emulsion cosmetic must contain the component (c2).

A case in which the emulsion cosmetic of the present invention contains the polyether-modified silicone having no alkyl chain (component (c2)) requires a condition in which the ratio of blending quantity of the component (c1) to that of the component (c2), i.e., [(c1)/(c2)], is 0.8 or more, preferably 0.9 or more, and more preferably 1.0 or more. The ratio of less than 0.8 may cause a decrease in emulsion stability. The upper limit of the ratio is not particularly limited, and is generally 10 or less, preferably 8 or less, and more preferably 5 or less.

Note that the (c) nonionic surfactant in the present invention may contain a silicone-based or hydrocarbon-based nonionic surfactant other than the polyether modified silicone having a C12-22 branched hydrocarbon chain (component (c1)) and the polyether modified silicone having no alkyl chain (component (c2)), as long as the above conditions are satisfied.

In the emulsion cosmetic of the present invention, the ratio of the total blending quantity of the component (c1) and the component (c2) to the blending quantity of the dimethyldistearylammonium hectorite (component (b)), i.e., [((c1)+(c2))/(b)], should be 2 or more, preferably 2.15 or more, and more preferably 2.3 or more, the ratio of the total blending quantity of the component (c1) and the component (c2) to the blending quantity of the fragrance material (component (a)), i.e., [((c1)+(c2))/(a)], should be 0.8 or more, preferably 0.9 or more, and more preferably 1.0 or more. Unless any of these conditions is satisfied, sufficient emulsion stability may sometimes not be exerted. The upper limits of these ratios are not particularly limited, and the upper limit for [((c1)+(c2))/(b)] is generally 10 or less, preferably 8 or less, and more preferably 5 or less, and the upper limit for [((c1)+(c2))/(a)] is 5 or less, preferably 4 or less, and more preferably 3 or less.

The emulsion cosmetic of the present invention can be prepared by forming a composite of (b) dimethyldistearylammonium hectorite and (c) nonionic surfactant in oil so as to form an oil gel, and then dispersing an aqueous phase therein.

The oils capable of forming an oil phase in the emulsion cosmetic of the present invention are not particularly limited, and examples thereof include, as animal and plant oils, natural animal and plant oils and fats such as avocado oil, camellia oil, macadamia nut oil, corn oil, evening primrose oil, mink oil, jojoba oil, rape seed oil, castor oil, sunflower oil, cacao oil, coconut oil, rice bran oil, olive oil, lanolin, and squalene, fatty acid esters such as liquid paraffin, squalane, isopropyl myristate, isopropyl palmitate, isopropyl stearate, glycerol 2-ethylhexanoate, glyceryl tri2-ethylhexanoate, and pentaerythrityl tetra-2-ethylhexanoate, polar oils such as diethyleneglycolmonopropylether, polyoxyethylene polyoxypropylene pentaerythritol ether, polyoxypropylene butyl ether, and ethyl linoleate, and silicone oils such as methyl polysiloxane, methylphenyl polysiloxane, methylhydrogen polysiloxane, decamethyl polysiloxane, methyl polysiloxane, octamethylcyclotetrasiloxane, dodecamethylcyclohexasiloxane, and highly polymerized methylpolysiloxane.

The emulsion cosmetic of the present invention contains as a nonionic surfactant, a silicone-based surfactant (component (c1) and an arbitrarily component (c2)), as a major component. However, oil to be blended therewith can constitute a stable emulsion system even if the oils do not include any silicone oil, and particularly any volatile silicone oil. This is a feature unpredictable from the invention of Patent document 2 wherein oils essentially include volatile silicone oil such as decamethylcyclopentasiloxane, for example, in the case of a water-in-oil emulsion thickened and stabilized by organic modified clay mineral and linear polyether modified silicone.

The thus prepared emulsion cosmetic of the present invention has a hardness of 6 or higher, preferably 8 or higher, and more preferably 10 or higher as measured using a rheometer at 25° C. (11.3 φ, 3 mm penetration). The emulsion cosmetic of the present invention having such hardness retains appropriate hardness without flowing when filled in a jar container, for example. The upper limit of hardness is not particularly limited, and is generally 30 or lower, preferably 25 or lower, and more preferably 20 or lower.

The emulsion cosmetic of the present invention can be blended with, in addition to the above examples, an arbitrary component that can be generally blended in a water-in-oil emulsion cosmetic, as long as the component does not inhibit the effects of the invention.

Examples of such an arbitrary component include UV absorbents such as para-aminobenzoic acid, homomethyl-7N-acetyl anthranilate, butyl methoxy benzoylmethane, glyceryl di-p-methoxycinnamate-mono-2-ethylhexanoate, amyl salicylate, octyl cinnamate, and 2.4-dihydroxybenzophenone, lower alcohols such as ethanol, moisturizers such as glycerin, 1,3-butylene glycol, polyethylene glycol, sorbitol, xylitol, and maltitol, thickeners such as agar, methylcellulose, gum arabic, and polyvinyl alcohol, antioxidants such as butylated hydroxytoluene, tocopherol, and phytic acid, antimicrobial preservatives such as benzoic acid, salicylic acid, sorbic acid, para-hydroxybenzonate (e.g., ethylparaben and butylparaben), and hexachlorophene, organic acids such as acyl sarcosinic acid (for example, sodium lauroylsarcosinate), glutathione, citric acid, malic acid, tartaric acid, and lactic acid, vitamin A and a derivative thereof, B vitamins such as vitamin B6 hydrochloride, vitamin B6 tripalmitate, vitamin B6 dioctanoate, vitamin B2 and a derivative thereof, vitamin B12, and vitamin B15 and a derivative thereof, C vitamins such as ascorbic acid, ascorbic acid sulfate ester (salt), ascorbic acid phosphate ester (salt), and ascorbic acid dipalmitate, E vitamins such as α-tocopherol, β-tocopherol, γ-tocopherol, vitamin E-acetate, and vitamin E-nicotinate, D vitamins, H vitamins, vitamins such as pantothenic acid and pantethine, various drugs such as nicotinic acid amide, benzyl nicotinate, γ-oryzanol, allantoin, glycyrrhizic acid (salt), glycyrrhetinic acid and a derivative thereof, hinokitiol, mucidin, bisabolol, eucalyptol, thymol inositol, pantothenyl ethylether, ethinyl estradiol, cepharanthine, and placenta extract, and pigments.

For example, blending of lower alcohol such as ethanol (preferably about 5 to 20% by mass) can improve the spreadability of the cosmetic, and blending of a thickener such as agar, methylcellulose, gum arabic, and polyvinyl alcohol (preferably about 0.5 to 5% by mass) can give richer sense of use.

The water-in-oil emulsion cosmetic of the present invention can be provided as highly flavored and scented (fragrant) cream, and can also be provided as a fragrance cosmetic having appropriate hardness.

EXAMPLES

The present invention is further described as follows in detail with reference to examples, but the present invention is not limited by these examples. Blending quantity is represented by "% by mass" of a component to be blended in a system, unless otherwise specified.

Water-in-oil emulsion cosmetics (cream) were prepared with the compositions listed in the following Tables 1 to 3.

The thus obtained cosmetics were evaluated for (1) rheometer hardness, (2) emulsion stability, and (3) freshness and spreadability in an actual use test.

Evaluation Method
(1) Hardness

Hardness measured under an atmosphere at 25° C. using a rheometer (manufactured by FUDO Kougyou, Inc.: NRM-3002D; diameter of 11.3 mm, 3 mm penetration) is shown in each table.

(2) Emulsion Stability

The cosmetic of each example was visually observed and evaluated on the basis of the following criteria.
 ○: Stable, and no changes was observed on appearance.
 x: Separation of emulsion was observed.

(3) Actual Use Test

Professional panelists used the sample of each example and evaluated based on the following criteria.
 S: Extremely good.
 A: Good.
 B: Slightly poor.
 C: Poor.

TABLE 1

| | | Reference example | Example 1 | Example 2 | Example 3 | Example 4 | Example 5 |
|---|---|---|---|---|---|---|---|
| Water | Water | Remainder | Remainder | Remainder | Remainder | Remainder | Remainder |
| Alcohol | 95% ethanol | — | — | — | — | — | — |
| Moisturizer | Glycerin | 2.5 | 2.5 | 2.5 | 2.5 | 2.5 | 2.5 |
| | 1,3-Butylene glycol | 7 | 7 | 7 | 7 | 7 | 7 |
| | Dipropylene glycol | 5 | 5 | 5 | 5 | 5 | 5 |
| | Polyethylene glycol 6000 | 2 | 2 | 2 | 2 | 2 | 2 |
| Thickener | Agar | — | — | — | — | — | — |
| | Dimethyldistearylammonium hectorite (b) | 2.1 | 2.1 | 2.1 | 2.1 | 2.1 | 2.1 |
| Surfactant | Methylpolysiloxane•cetylmethyl polysiloxane•poly(oxyethylene(oxypropylene)methyl-polysiloxane copolymer (c1) | 2 | 5 | 2.5 | 2.5 | 3 | 3 |
| | PEG-9 polydimethylsiloxyethyl dimethicone (c2) | 2 | — | 2.5 | — | 3 | 3 |
| | PEG-10 dimethicone (c2) | — | — | — | 2.5 | — | — |

TABLE 1-continued

|  |  | Reference example | Example 1 | Example 2 | Example 3 | Example 4 | Example 5 |
|---|---|---|---|---|---|---|---|
| Oil | Isododecane | 3 | 3 | 3 | 3 | 3 | 3 |
|  | Methyl polysiloxane(6CS) | 3.5 | 3.5 | 3.5 | 3.5 | 3.5 | 3.5 |
|  | α-olefin oligomer | 1.5 | 1.5 | 1.5 | 1.5 | 1.5 | 1.5 |
|  | 2-Ethylhexanoic acid cetyl | 1.5 | 1.5 | 1.5 | 1.5 | 1.5 | 1.5 |
| Drug | Acetylated hyaluronic acid | 0.002 | 0.002 | 0.002 | 0.002 | 0.002 | 0.002 |
|  | Rose extract | 0.01 | 0.01 | 0.01 | 0.01 | 0.01 | 0.01 |
| Preservative | Phenoxyethanol | 0.3 | 0.3 | 0.3 | 0.3 | 0.3 | 0.3 |
| Chelating reagent | Edetate a sodium | 0.1 | 0.1 | 0.1 | 0.1 | 0.1 | 0.1 |
| Stabilizing agent | Sodium carboxymethyl cellulose | 0.1 | 0.1 | 0.1 | 0.1 | 0.1 | 0.1 |
|  | Sodium chloride | 1 | 1 | 1 | 1 | 1 | 1 |
| Powder | Silicic anhydride | 2 | 2 | 2 | 2 | 2 | 2 |
| Pearl agent | Pearl agent | 0.62 | 0.62 | 0.62 | 0.62 | 0.62 | 0.62 |
| Color agent | Blue No. 1 | 0.0004 | 0.0004 | 0.0004 | 0.0004 | 0.0004 | 0.0004 |
| Fragrance | Mixed fragrance materials of limonene 30% + undecylaldehyde35% phenylethyl alcohol35% (a) | — | 5 | 5 | 5 | 5 | 7 |
|  | (c1) + (c2)/(b) | 1.9 | 2.38 | 2.38 | 2.38 | 2.86 | 2.86 |
|  | (c1) + (c2)/(a) | — | 1 | 1 | 1 | 1.2 | 0.86 |
|  | (c1)/(c2) | 1 | — | 1 | 1 | 1 | 1 |
|  | Hardness (11.3φ 25° C.) | 20 | 11 | 11 | 11 | 13 | 10 |
|  | Emulsion stability | ○ | ○ | ○ | ○ | ○ | ○ |
|  | Freshness | A | A | A | A | A | A |
|  | Spreadability | A | A | A | A | A | A |

TABLE 2

|  |  | Comparative example 1 | Comparative example 2 | Comparative example 3 | Comparative example 4 | Comparative example 5 | Comparative example 6 |
|---|---|---|---|---|---|---|---|
| Water | Water | Remainder | Remainder | Remainder | Remainder | Remainder | Remainder |
| Alcohol | 95% ethanol | — | — | — | — | — | — |
| Moisturizer | Glycerin | 2.5 | 2.5 | 2.5 | 2.5 | 2.5 | 2.5 |
|  | 1,3-Butylene glycol | 7 | 7 | 7 | 7 | 7 | 7 |
|  | Dipropylene glycol | 5 | 5 | 5 | 5 | 5 | 5 |
|  | Polyethylene glycol 6000 | 2 | 2 | 2 | 2 | 2 | 2 |
| Thickener | Agar | — | — | — | — | — | — |
|  | Dimethyldistearylammonium hectorite (b) | 1.2 | 2.1 | 2.1 | 2.1 | 2.1 | 2.1 |
| Surfactant | Methylpolysiloxane•cetylmethyl polysiloxane•poly(oxyethylene• oxypropylene)methylpolysiloxane copolymer (c1) | 2 | 2 | 2 | — | 3 | 2.5 |
|  | PEG-9 polydimethylsiloxyethyl dimethicone (c2) | 2 | 2 | 3 | 5 | 3 | 3.5 |
|  | PEG-10dimethicone (c2) | — | — | — | — | — | — |
| Oil | Isododecane | 3 | 3 | 3 | 3 | 3 | 3 |
|  | Methyl polysiloxane(6CS) | 3.5 | 3.5 | 3.5 | 3.5 | 3.5 | 3.5 |
|  | α-Olefin oligomer | 1.5 | 1.5 | 1.5 | 1.5 | 1.5 | 1.5 |
|  | Cetyl 2-ethylhexanoate | 1.5 | 1.5 | 1.5 | 1.5 | 1.5 | 1.5 |
| Drug | Acetylated hyaluronic acid | 0.002 | 0.002 | 0.002 | 0.002 | 0.002 | 0.002 |
|  | Rose extract | 0.01 | 0.01 | 0.01 | 0.01 | 0.01 | 0.01 |
| Preservative | Phenoxyethanol | 0.3 | 0.3 | 0.3 | 0.3 | 0.3 | 0.3 |
| Chelating reagent | Edetate trisodium | 0.1 | 0.1 | 0.1 | 0.1 | 0.1 | 0.1 |
| Stabilizing agent | Sodium carboxymethyl cellulose | 0.1 | 0.1 | 0.1 | 0.1 | 0.1 | 0.1 |
|  | Sodium chloride | 1 | 1 | 1 | 1 | 1 | 1 |
| Powder | Silicic anhydride | 2 | 2 | 2 | 2 | 2 | 2 |
| Pearl agent | Pearl agent | 0.62 | 0.62 | 0.62 | 0.62 | 0.62 | 0.62 |
| Color agent | Blue No. 1 | 0.0004 | 0.0004 | 0.0004 | 0.0004 | 0.0004 | 0.0004 |
| Fragrance | Mixed fragrance materials of limonene 30% + undecylaldehyde35% phenylethyl alcohol35% (a) | 5 | 5 | 5 | 5 | 8.1 | 7 |
|  | (c1) + (c2)/(b) | 3.33 | 1.9 | 2.38 | 2.38 | 2.86 | 2.86 |
|  | (c1) + (c2)/(a) | 0.8 | 0.8 | 1 | 1 | 0.74 | 0.86 |
|  | (c1)/(c2) | 1 | 1 | 0.67 | 0 | 1 | 0.71 |
|  | Hardness (11.3φ 25° C.) | 10 | 10 | 11 | 11 | 10 | 10 |
|  | Emulsion stability | X | X | X | X | X | X |
|  | Freshness | A | A | A | A | A | A |
|  | Spreadability | A | A | A | A | A | A |

As shown in Reference Example in Table 1, when no fragrance material was blended, a water-in-oil emulsion stabilized by dimethyldistearylammonium hectorite and a nonionic surfactant was obtained. When fragrance material was blended in 5 mass % or more in the system and the compositions, the ranges of the blending quantities and the ratios of the blending quantities of the fragrance material (component (a)), dimethyldistearylammonium hectorite (component (b)) and the nonionic surfactant ((c) component) satisfied the conditions of the present invention, cosmetics excellent in emulsion stability and usability (Examples 1 to 5) were obtained, although slight decreases were observed in hardness.

However, as shown in Table 2, it was confirmed that a stable emulsion was not obtained when the blending quantity of dimethyldistearylammonium hectorite (component (b)) was less than 1.5 mass % (Comparative example 1), when a nonionic surfactant contained no polyether modified silicone (c1) having a C12-22 branched hydrocarbon chain (Comparative example 4), when the ratio of the total blending quantity of polyether modified silicone (c1) having a C12-22 branched hydrocarbon chain and polyether modified silicone (c2) having no alkyl chain to the blending quantity of fragrance material (component (a)) or dimethyldistearylammonium hectorite (component (b)) did not satisfy the conditions (Comparative examples 2 and 5), and further when the ratio of the blending quantity of the component (c1) to that of the component (c2) did not satisfy the conditions (Comparative examples 3 and 6).

As in the results shown in Table 3, it can be confirmed that even if the type or the blending quantity of fragrance materials is varied, a stable water-in-oil emulsion cosmetic maintaining appropriate hardness can be obtained, as long as they satisfy the conditions of the present invention. In addition, limonene is a fragrance material with low polarity, phenylethyl alcohol is a fragrance material with high polarity, and undecyl aldehyde is a fragrance material having intermediate polarity between the two.

Furthermore, as in the results obtained in Examples 9 and 10 in Table 3, it is confirmed that addition of ethanol to the emulsion cosmetic of the present invention further improves spreadability, and blending with agar further improves a fresh feel.

The invention claimed is:

1. A water-in-oil emulsion cosmetic, comprising:
    (a) 5 to 15% by mass of a fragrance material;
    (b) 1.5 to 3% by mass of dimethyldistearylammonium hectorite; and
    (c) a nonionic surfactant;
    wherein, said (c) nonionic surfactant comprises:
        (c1) a polyether-alkyl-comodified silicone having a C12-22 alkyl chain in the amount of 2 to 10% by mass relative to the total weight of said cosmetic;
        wherein said polyether-alkyl-comodified silicone having a C12-22 alkyl chain (c1) is at least one selected from a group consisting of polyether-alkyl-comodified silicones represented by the following formula (I):

TABLE 3

| | | Example 6 | Example 7 | Example 8 | Example 9 | Example 10 |
|---|---|---|---|---|---|---|
| Water | Water | Remainder | Remainder | Remainder | Remainder | Remainder |
| Alcohol | 95% ethanol | — | — | — | 10 | 10 |
| Moisturizer | Glycerin | 2.5 | 2.5 | 2.5 | 2.5 | 2.5 |
| | 1,3-butylene glycol | 7 | 7 | 7 | 7 | 7 |
| | Dipropylene glycol | 5 | 5 | 5 | 5 | 5 |
| | Polyethylene glycol 6000 | 2 | 2 | 2 | 2 | 2 |
| Thickener | Agar | — | — | — | — | 1 |
| | Dimethyldistearylammonium hectorite (b) | 2.1 | 2.1 | 2.1 | 2.1 | 2.1 |
| Surfactant | Methyl polysiloxane•cetylmethyl polysiloxane•poly(oxyethylene•oxypropylene)methyl polysiloxane copolymer (c1) | 5 | 5 | 5 | 5 | 5 |
| | PEG-9 polydimethylsiloxyethyl dimethicone (c2) | 3 | 3 | 3 | 3 | 3 |
| Oil | Isododecane | 3 | 3 | 3 | 3 | 3 |
| | Methyl polysiloxane (6CS) | 3.5 | 3.5 | 3.5 | 3.5 | 3.5 |
| | α-Olefin oligomer | 1.5 | 1.5 | 1.5 | 1.5 | 1.5 |
| | Cetyl 2-ethylhexanoate | 1.5 | 1.5 | 1.5 | 1.5 | 1.5 |
| Agent | Acetylated hyaluronic acid | 0.002 | 0.002 | 0.002 | 0.002 | 0.002 |
| | Rose extract | 0.01 | 0.01 | 0.01 | 0.01 | 0.01 |
| Preservative | Phenoxyethanol | 0.3 | 0.3 | 0.3 | 0.3 | 0.3 |
| Chelating reagent | Edetate trisodium | 0.1 | 0.1 | 0.1 | 0.1 | 0.1 |
| Stabilizing agent | Sodium carboxymethyl cellulose | 0.1 | 0.1 | 0.1 | 0.1 | 0.1 |
| | Sodium chloride | 1 | 1 | 1 | 1 | 1 |
| Powder | Silicic anhydride | 2 | 2 | 2 | 2 | 2 |
| Pearl agent | Pearl agent | 0.62 | 0.62 | 0.62 | 0.62 | 0.62 |
| Color agent | Blue No. 1 | 0.0004 | 0.0004 | 0.0004 | 0.0004 | 0.0004 |
| Fragrance | Mixed fragrance materials of limonene 30% + undecylaldehyde35% phenylethyl alcohol35% (a) | — | — | — | 8.1 | 8.1 |
| | Limonene (a) | 7 | — | — | — | — |
| | Undecylaldehyde (a) | — | 7 | — | — | — |
| | Phenylethylalcohol (a) | — | — | 7 | — | — |
| | (c1) + (c2)/(b) | 3.81 | 3.81 | 3.81 | 3.81 | 3.81 |
| | (c1) + (c2)/(a) | 1.14 | 1.14 | 1.14 | 0.99 | 0.99 |
| | (c1)/(c2) | 1.67 | 1.67 | 1.67 | 1.67 | 1.67 |
| | Hardness (11.3φ 25° C.) | 12 | 11 | 12 | 12 | 15 |
| | Emulsion stability | ○ | ○ | ○ | ○ | ○ |
| | Freshness | A | A | A | A | S |
| | Spreadability | A | A | A | S | S |

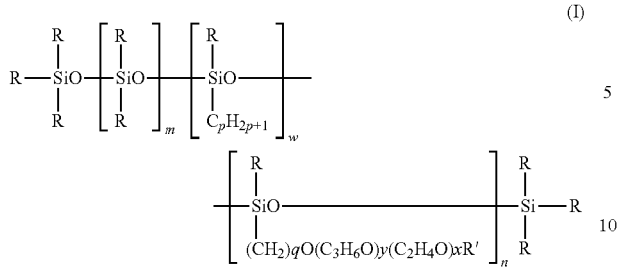
(I)

(in the above formula (I),
R is a C1-3 alkyl group or a phenyl group;
R' is hydrogen or a C1-12 alkyl group;
p ranges from 12 to 22;
q ranges from 1 to 50;
m ranges from 1 to 100;
n, w and x range respectively from 1 to 50; and
y ranges from 0 to 50); and (c2) a polyether modified silicone having no alkyl chain in the amount of at most 10% by mass relative to the total weight of said cosmetic
wherein said polyether modified silicone having no alkyl chain (c2) is at least one selected from a group consisting of polyether modified silicones represented by the following formula (II);

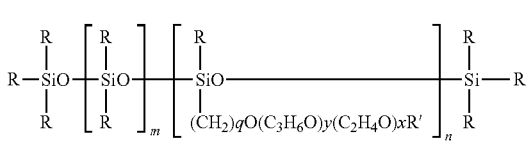
(II)

(in the above formula (II),
R is a C1-3 alkyl group or a phenyl group;
R' is hydrogen or a C1-12 alkyl group;
q ranges from 1 to 50;
m ranges from 1 to 100;
n and x range respectively from 1 to 50; and
y ranges from 0 to 50);

wherein
a ratio of a total blending quantity of said component (c1) and said component (c2) relative to a blending quantity of said component (b), i.e., [((c1)+(c2))/(b)], is at least 2;
a ratio of said total blending quantity of said component (c1) and said component (c2) to a blending quantity of said component (a), i.e., [((c1)(c2))/(a)], is at least 0.8;
said total blending quantity of said component (c1) and said component (c2) is at least 4% by mass relative to the total weight of said cosmetic;
a ratio of a blending quantity of said component (c1) to that of said component (c2), i.e., [(c1)/(c2)], is at least 0.8; and
said cosmetic has a hardness of at least 6 as measured using a rheometer (11.3 φ, 3 mm penetration) at 25° C.

2. The cosmetic according to claim 1, wherein:
said polyether-alkyl-comodified silicone having a C12-22 alkyl chain (c1) is a copolymer of methyl polysiloxane.cetylmethyl polysiloxane-poly(oxyethylene-oxypropylene)methyl polysiloxane.

3. The cosmetic according to claim 1, wherein:
said polyether modified silicone having no alkyl chain (c2) is at least one selected from a group consisting of PEG-9 polydimethylsiloxyethyl dimethicone and PEG-10 dimethicone.

4. The cosmetic according to claim 2, wherein:
said polyether modified silicone having no alkyl chain (c2) is at least one selected from a group consisting of PEG-9 polydimethylsiloxyethyl dimethicone and PEG-10 dimethicone.

* * * * *